US005176634A

United States Patent [19]

Smith et al.

[11] Patent Number: 5,176,634

[45] Date of Patent: Jan. 5, 1993

[54] FLEXIBLE MULTIPLE COMPARTMENT DRUG CONTAINER

[75] Inventors: Steven L. Smith; H. T. Young, both of El Toro, Calif.

[73] Assignee: McGaw, Inc., Irvine, Calif.

[21] Appl. No.: 561,917

[22] Filed: Aug. 2, 1990

[51] Int. Cl.[5] .............................................. A61M 37/00

[52] U.S. Cl. ........................................ 604/87; 604/89; 604/410; 604/416; 206/219; 206/221

[58] Field of Search ..................... 604/82, 87, 410, 56, 604/88-92, 408, 409, 416; 206/219, 221

[56] References Cited

U.S. PATENT DOCUMENTS

| | | | |
|---|---|---|---|
| 2,663,298 | 12/1953 | Rose . | |
| 3,257,072 | 6/1966 | Reynolds . | |
| 3,520,471 | 7/1970 | Faust | 604/410 X |
| 3,537,605 | 11/1970 | Solowey . | |
| 3,563,415 | 2/1971 | Ogle . | |
| 3,715,189 | 2/1973 | Nighohossian et al. . | |
| 3,726,276 | 4/1973 | Schumann et al. | 604/92 |
| 3,749,620 | 7/1973 | Montgomery | 206/219 X |
| 3,857,392 | 12/1974 | Ogle . | |
| 4,396,383 | 8/1983 | Hart | 604/56 |
| 4,410,321 | 10/1983 | Pearson et al. | 604/56 |
| 4,432,763 | 2/1984 | Manschot et al. | 604/262 |
| 4,443,219 | 4/1984 | Meisch et al. | 604/317 |
| 4,458,811 | 6/1984 | Wilkinson | 206/219 |
| 4,465,488 | 8/1984 | Richmond et al. | 604/414 |
| 4,467,588 | 8/1984 | Carveth | 53/425 |
| 4,484,920 | 11/1984 | Kaufman et al. | 604/416 |
| 4,515,586 | 5/1985 | Mendenhall et al. | 604/87 |
| 4,519,499 | 5/1985 | Stone et al. | 206/219 |
| 4,548,023 | 10/1985 | Danby et al. | 53/452 |
| 4,548,606 | 10/1985 | Larkin | 604/414 |
| 4,550,825 | 11/1985 | Sutryn et al. | 206/222 |
| 4,583,971 | 4/1986 | Bocquet et al. | 604/82 |
| 4,602,910 | 7/1986 | Larkin | 604/87 |
| 4,606,734 | 8/1986 | Larkin et al. | 604/84 |
| 4,607,671 | 8/1986 | Aalto et al. | 141/329 |
| 4,608,043 | 8/1986 | Larkin | 604/87 |
| 4,610,684 | 9/1986 | Knox et al. | 604/416 |
| 4,614,267 | 9/1986 | Larkin | 206/221 |
| 4,629,080 | 12/1986 | Carveth | 215/11 R |
| 4,731,053 | 3/1988 | Hoffman | 604/89 |
| 4,770,295 | 8/1988 | Carveth et al. | 206/219 |
| 4,781,679 | 11/1988 | Larkin | 604/88 |
| 4,994,056 | 2/1991 | Ikeda | 604/410 |
| 4,997,083 | 3/1991 | Loretti et al. | 206/219 |
| 8,985,135 | 10/1976 | Carpenter et al. | 604/410 |

*Primary Examiner*—C. Fred Rosenbaum
*Assistant Examiner*—Mark O. Polutta
*Attorney, Agent, or Firm*—Christie, Parker & Hale

[57] ABSTRACT

A flexible container is provided for the storage and mixing together of diluents and medicaments. The container incorporates multiple compartments, separated by frangible seals, in which the diluents and medicaments are stored. The seals are ruptured by manipulation of the container to thereby mix the contents together for delivery through a standard IV arrangement to a patient.

19 Claims, 6 Drawing Sheets

FLEXIBLE MULTIPLE COMPARTMENT DRUG CONTAINER

FIELD OF THE INVENTION

The present invention relates to the field of IV fluid containers for storage and combination of diluents and medicaments. More particularly, the invention provides a single flexible container having multiple compartments to separately contain a diluent and a medicament for storage. The compartments are separated by frangible seals which may be ruptured by manipulation of the container to mix the contents and to deliver the contents through a port to a standard IV arrangement.

BACKGROUND OF THE INVENTION

There exists an ongoing need for the development and improvement of containers for the administration of IV liquids in chemical or drug therapies, nutritional supplements and blood transfusions. Particularly, in the field of chemical and drug therapies, the IV solution delivered to the patient often comprises a mixed combination of a diluent and one or more medicaments. In many cases, the medicaments must be maintained separately from the diluent until immediately before use to prevent degradation. Common packaging of the diluent and medicaments is often further complicated by the character of the medicament which may be a powder sensitive to moisture contamination, or a powder or liquid sensitive to degradation under light or oxygen exposure.

Numerous recent improvements in the technology of IV containers have been made providing flexible containers which are less easily damaged and more easily stored and handled. Containers such as that disclosed in U.S. Pat. Nos. 4,458,811 to Wilkinson and 4,608,043 to Larkin are representative of prior art multiple compartment flexible containers allowing separate storage of medicaments and diluents which may be mixed immediately prior to use. A second type of prior art devices provide a flexible diluent container with an attachment means for a second container containing a medicament and integral systems for engagement of the containers to maintain sterility while mixing the components.

Alternate systems in the prior art include combined containers wherein an inner container is physically manipulated from the exterior of a flexible covering container to release a medicament for mixing with a diluent in the flexible container. A vial contained within the flexible container having a plug or lid which may be extracted from the vial by manipulating the vial through the flexible walls of the container is exemplified in U.S. Pat. No. 4,610,684 to Knox et al. An additional alternative is provided in the prior art by pre-mixing the medicament and diluent and freezing the container until ready for use to extend shelf life by preventing degradation of the pre-mixed solution. The complexities and disadvantages are self evident of numerous and complicated parts for the containers or the added requirement for refrigeration support devices of these prior art approaches.

Further improvement over the prior art containers is desireable in that sealing mechanisms between compartmented containers such as that disclosed in Wilkinson have been complex and costly. Similarly, interconnecting devices for combination of two containers or for mechanical puncturing and interconnection of joined containers require numerous components which are expensive to fabricate and increase the possibility of failure. In addition, the dispensing configuration of prior art containers may preclude complete emptying of the container or require the presence of significant quantities of air in the container to allow complete delivery of the fluid contents of the container. Presence of significant quantities of air in the sealed container may produce difficulties during sterilization of the containers since air expansion at the sterilization temperatures may damage the flexible material of the container. Finally, configuration of multi-compartmented prior art containers has, in many cases, precluded assurance of complete mixing of medicaments with diluents prior to delivery to the patient.

It is therefore desirable to provide an IV container having multiple compartments for storage of diluent and medicaments in a single package having simple frangible seals dividing the compartments which may be ruptured for combination and mixing of the contents. It is further desirable that the container arrangement preclude the inadvertent delivery of any of the components prior to mixing and allow visual verification of condition of the components prior to mixing and after mixing is complete, before dispensing. It is also desireable that the contents of the container be completely deliverable to the patient without the requirement for the presence of a significant quantity of air in the container. The capability for enhanced protection of the contents in one or more of the compartments of the container against moisture or oxygen permeation or light degradation is also desirable.

SUMMARY OF THE INVENTION

The present invention provides the desired features with a container having multiple compartments separated by peelable seals which may be ruptured by manually applying pressure to the exterior of the container. The container is formed of two sheets of flexible materials which are sealed at their perimeter. Separate compartments in the container are formed by frangible heat seals. In a first embodiment of the invention, three compartments are formed in the container; a first compartment contains a liquid diluent, a second compartment contains a powdered medicament which may be mixed with the liquid diluent by separating the frangible seal dividing the two compartments. Separating of the seal is accomplished by manipulating the container to create pressure on the diluent in the first compartment which then hydraulically separates the seal between the compartments allowing the diluent and medicament to be mixed. A third compartment adjacent the second compartment and opposite from the diluent compartment contains an outlet port for dispensing the mixed fluid. A seal between the second and third compartment prevents administration of the contents before mixing of the contents of the first two compartments. After mixing, additional manipulation of the container to exert pressure on the contents ruptures the second seal allowing the medicated fluid to be dispensed through the port.

The flexible materials of the sheets forming the container are selected based on requirements of the contained diluents and medicaments. In a first embodiment, a front sheet is a transparent multi-layer laminate having an inner layer of low melting temperature polypropylene and an outer layer of a higher melting temperature polypropylene. The rear sheet is impermeable to water vapor and comprises a laminated material having an inner layer of polypropylene, a middle layer of aluminum foil and an outer layer of polyester film. Vapor impermeability of the rear sheet extends the shelf life of the product by reducing by half the permeation of diluent vapor from the container and permeation into the medicament, if a powder, of vapor from the atmosphere. If additional reduction in vapor permeability is required for the medicament compartment, a third sheet of laminated material which, in one embodiment, is identical to the rear sheet and sized to cover the medicament compartment may be affixed over the front sheet in the region of the medicament compartment to provide a vapor impermeable enclosure.

The frangible or peelable seals between the compartments in the container are formed using a hot bar technique sealingly adhering the interfacing polypropylene layers of the front and rear sheet. Attachment of the third sheet to the medicament compartment may be accomplished also using a hot bar technique adheringly sealing the inner polypropylene layer of third sheet to the outer polypropylene layer of the front sheet. The third sheet may subsequently be peelably removed at the time of use to expose the medicament for visual inspection prior to mixing.

An outlet port is mounted in the transparent front sheet in the region of the third compartment by inserting the port through an aperture in the sheet sized to receive the port with an overlapping engagement of a perimeter flange and the inner layer of the sheet which may then be heat sealed. Arrangement of the outlet port in the front sheet of the container allows collapse of the rear sheet of the container against the front sheet to fully drain the container and avoid any requirement for introduction of significant quantities of air into the container to allow complete dispensing.

BRIEF DESCRIPTION OF THE DRAWINGS

These and other features, aspects and advantages of the present invention will be more fully understood when considered with regard to the following detailed description, appended claims and accompanying drawings wherein:

DETAILED DESCRIPTION OF THE INVENTION

Figure 1:
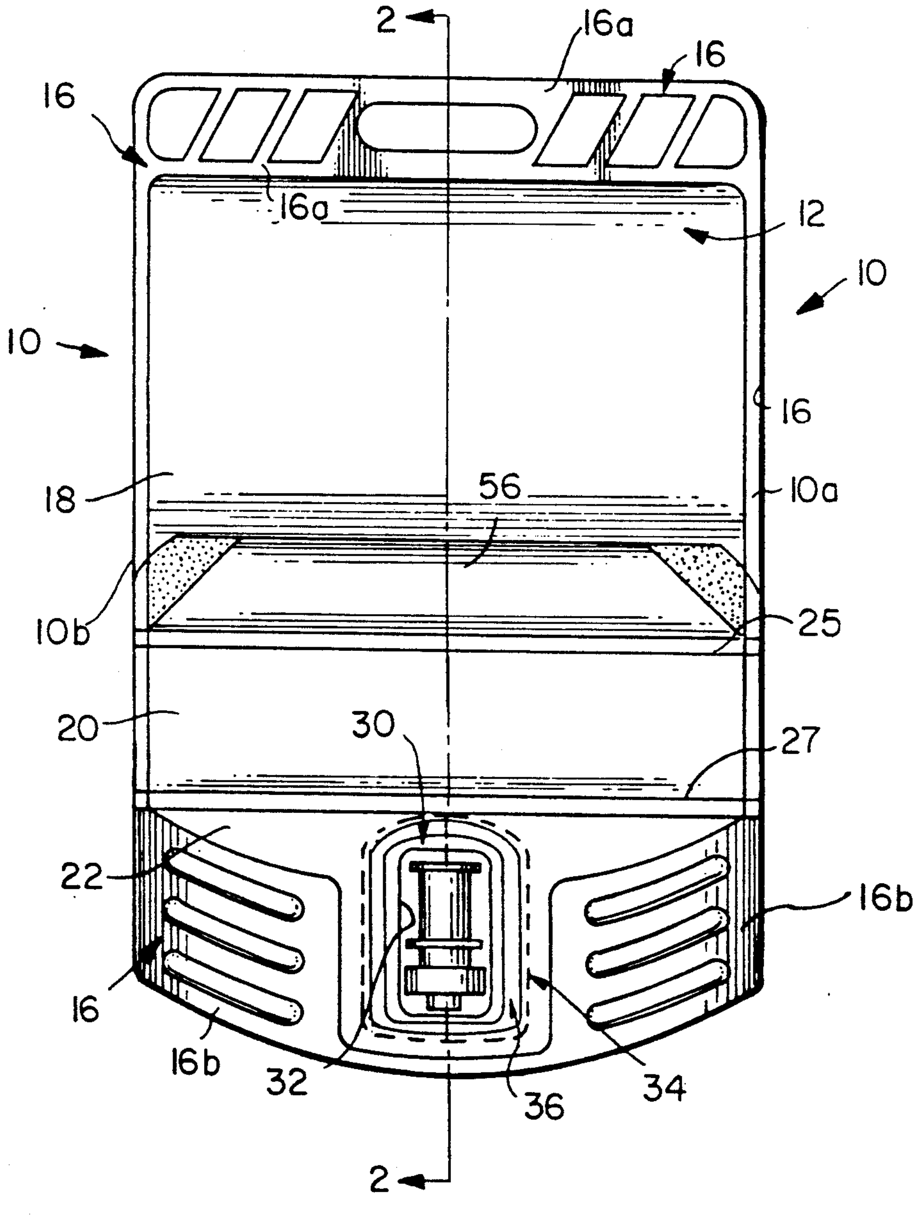
FIG. 1 is a semi-schematic front view of one exemplary embodiment of a container provided in accordance with practice of the present invention showing the arrangement of the compartments and intervening seals including the outlet port.
Figure 2:
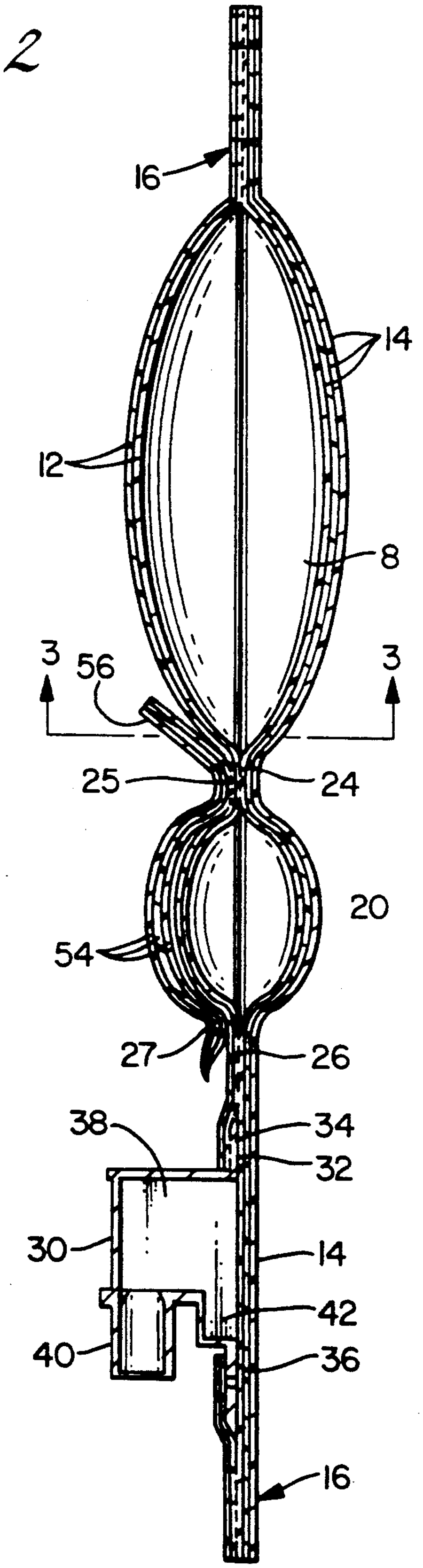
FIG. 2 is a semi-schematic side cross section view taken along line 2—2 of FIG. 1 showing the flexible sheets forming the container and the orientation and configuration of the outlet port, thickness of the layers in the sheets is exaggerated for clarity.

Referring to FIGS. 1 and 2, there is shown an exemplary embodiment of a container 10 provided in accordance with practice of principles of this invention. Although the container 10 can be viewed in any orientation, for purposes of explanation herein, the position of the components of the container relative to each other are described as positioned in FIGS. 1 and 2. The container 10 is formed from a front sheet 12 and a back or rear sheet 14 which may be laminates of flexible materials to be described in greater detail subsequently. The sheets forming the container are sealed together at their common peripheral edge forming an edge seal 16 which extends around the entire periphery of the container. Such peripheral seals may vary in configuration and width. A patterned seal such as that shown for the top seal **16*a* and the bottom seal 16*b* in FIG. 1** may be used to provide grasping areas for the user to handle the container and for the attachment to IV support stands.

The container 10 is partitioned into three separate compartments in the embodiment shown. An upper compartment 18, an intermediate compartment 20 and a lower compartment 22. As shown in FIG. 2, the upper and intermediate compartments are separated by a first peelable seal 24 and the intermediate and lower compartments are separated by a second peelable seal 26. The peelable seals extend between the two sides of the container, right side **10*a* and left side 10*b*, joining the front and rear sheets. A "peelable seal" as used herein is a seal which is sufficiently durable to allow normal handling of the container yet which will peel or separate substantially completely from the right side to the left side under pressure applied by manipulating the container thereby allowing mixing and dispensing of the container contents. A peelable seal is formed by a partial melting together of the polymer present in the adjacent layers of the front and back sheets. The seal is obtained by heat sealing with varying times, temperatures and pressures to be described in greater detail subsequently. Conversely, the peripheral edge seal 16** is significantly stronger than the "peelable seals" and will not be ruptured by pressures generated to separate the peelable seals. Configuration of the peelable seals as a straight line between the peripheral seals as opposed to a chevron design or the like, promotes substantially complete peeling of the entire seal during use of the container as will be described in greater detail subsequently.

In a typical application for the container 10 of the present invention, the upper compartment 18 is filled with a liquid diluent and the intermediate compartment 20 is filled with a medicament. The lower compartment 22 provides the interface for an outlet port 30 and remains empty until the container is used. The outlet port extends through an aperture 32 in the front sheet 12 of the container 10. A flange 34, best seen in FIG. 2, on the outlet port engages the inner surface of the front sheet around the periphery of the aperture which may be heat sealed to the flange forming an outlet seal 36. The outlet port 30 comprises a body portion 38 and a nozzle 40 which is attachable to a standard IV administration device. As best seen in FIG. 2, the configuration of the outlet port 30 allows the rear sheet 14 to collapse fully against the front sheet and flange 34 of the outlet port 30. Also, external air pressure on the front and rear sheets of the container tends to force the front and rear sheets of the container 10 together during dispensing of the contents. This combination of features allows the contents of the container to be fully dispensed with only a small quantity of the solution remaining in the ullage space 42 of the outlet port 30. In the embodiment shown, this ullage results from the molding process employed for forming the outlet port. Additional ullage may arise depending on configuration of the IV attachment or "spike" and positioning of a sterile sealing diaphragm typically located at the top of the cylindrical nozzle 40. Alternate forming methods leaving no ullage may be employed to allow complete draining of the container. The combination of outlet port configuration and general configuration of the container precludes a requirement for presence of substantial quantities of air within the container to allow complete draining of the solution to be administered.

The materials employed in the front and rear sheets of the container 10 are selected based on the material to be stored. Preferably, at least one of the sheets is transparent to allow the contents of the container to be visually inspected and to allow the level of the solution in the container to be seen during dispensing. Typically, the front sheet 12 is transparent. Suitable materials for fabrication of the front sheet are typically laminated, multilayer films. Examples of such films are disclosed in U.S. Pat. No. 4,803,102 to Raniere et al., the disclosure of which is incorporated herein by reference.

Figure 3:
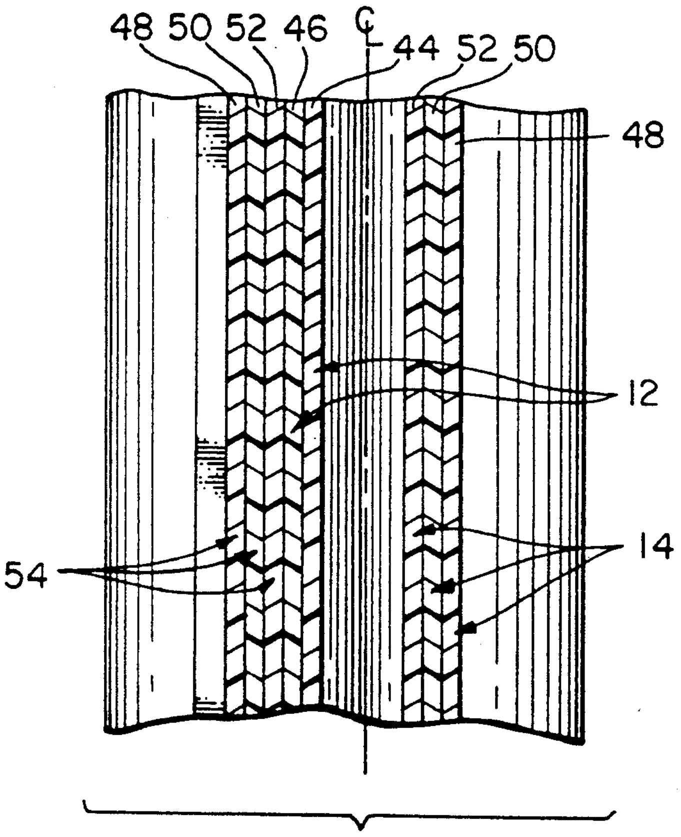
FIG. 3 is a semi-schematic cutaway view along line 3—3 of FIG. 2 showing the laminate configuration of the flexible sheets employed in the container.

Referring particularly to FIG. 3, a laminate employed as the front sheet 12 in one exemplary embodiment of the container 10 comprises a transparent thermoplastic polymer laminate having an inner polymer seal layer 44 and an outer higher temperature polymer layer 46. Polypropylene or polyethylene or combinations of the two can be used as the polymer. In one embodiment, the inner or seal layer comprises a blend of about 80% polypropylene polyethylene copolymer available from Fina Oil and Chemical Company, Deerpark, TX having a commercial designation of Z9450 and 20% styrene butadiene elastomer rubber available from Shell Chemical Corporation under the trademark "Kraton" and having a commercial designation G1652. The outer high temperature layer 46 is a high ethylene content random copolymer available from Fina having a commercial designation 7450. In one embodiment, the inner layer 44 of the 80%/20% polypropylene copolymer and styrene butadiene elastomer is 7 mils thick while the outer layer 46 of the higher temperature polypropylene is 1 mil in thickness. Other thicknesses can be provided, as described.

For certain combinations of diluents and medicaments, the rear sheet 14 can have the same composition and configuration as the front sheet 12. Considerations of shelf life and susceptibility to vapor permeability into or out from the container 10 may require the use of an alternate material for the rear sheet. In the embodiment of the container shown in the drawings (FIG. 3), a rear sheet 14 is employed which is impermeable to water vapor to increase shelf life. The rear sheet comprises a three layer laminate including an aluminum foil. One such suitable laminate is a commercially available product from Reynolds Aluminum designated "Flex Can II RT" which includes an outer layer 48 of polyester, a middle layer 50 of aluminum foil and an inner seal layer 52 of polypropylene. The individual layers of the "Flex Can" laminate are adhesively bonded to each other using 2.5 pounds per ream adhesive between the outer layer and aluminum foil and a 1.0 pound per ream adhesive between the aluminum foil and inner polypropylene seal layer. Typical dimensions of the "Flex Can II" laminate are 0.48 mil for the outer polyester layer, 0.7 mil for the aluminum foil and 3.0 mil for the polypropylene layer.

Embodiments that have been fabricated indicate that preferable material choices for the front and rear sheets to optimize the performance of the peelable seals incorporate an interfacing seal layer on one sheet comprising a blend incorporating a polymer and styrene butadiene elastomer blend for the interfacing layer and the opposing interfacing layer on the mating sheet comprising a polymer layer without the elastomer. Alternatively, the interfacing layers of the front and rear sheets comprise polymer and styrene butadiene elastomer blends having differing percentages of the styrene butadiene elastomer. Table I is a non-limiting list showing seven examples of single and multiple layer films or laminates useful in fabrication of various embodiments of the invention.

TABLE I

Description of film structures for front and rear sheets:

| Designator | | |
|---|---|---|
| 1. S62-71 | Outside Layer: | 1 Mil Fina 7450XAC PP/PE random copolymer |
| | Interface Layer: | 7 Mil 20% Kraton/80% Fina Z9450 blend |
| 2. S62-75 | Single Layer: | Fina Z-9450 |
| 3. Z4660 | Single Layer: | Horizon Z-4660 20% blend* |
| 4. S62-100 | Outside Layer: | 1.2 mil ECDEL 9967** Copolyester |
| | Tie Layer: | .8 mil Kraton G1652 |
| | Interface Layer: | 6.2 mil 30% Kraton/70% Fina Z9450 blend |
| 5. S62-101 | Outside Layer: | 1.2 mil ECDEL 9967 Copolyester |
| | Tie Layer: | .8 mil Kraton G1652 |
| | Interface Layer: | 6.2 mil 40% Kraton/60% Fina Z9450 blend |
| 6. X62-053 | Single Layer: | 8 mil Fina 7450AC PP/PE Random Copolymer |
| 7. Foil | Reynolds Flex Can II RT | |

*Denotes a product of Horizon Polymers, a Division of Ferro Corporation, Houston, TX. Blend contains a thermoplastic elastomer other than styrene butadiene.
**"ECDEL" is a trademark of Eastman Chemical Co. of Kingsport, Tenn.

In certain applications, particularly where the medicament is a powder, additional protection for the second or intermediate compartment 20 of the container 10 to preclude vapor transmission and degradation of the powder is desired. Referring particularly to FIGS. 2 and 3, in the illustrated embodiment, a third sheet 54 is employed to cover the intermediate compartment 20. In an exemplary embodiment, the composition of the third or cover sheet is identical to the rear sheet 14 and comprises a laminate including aluminum foil. The use of the aluminum foil laminate further provides protection from degradation of the medicament due to light exposure. The aluminum layer in the third sheet 54 and rear sheet prevents penetration of UV and visible spectrum light into the intermediate compartment 20 of the container.

Preferably the third sheet 54 can be removed from the container prior to its use to allow examination of the powder medicament. In one embodiment, best seen in FIGS. 2 and 4, the third sheet 54 includes a tab 56 which may be grasped to peel the third sheet from the transparent front sheet 12 so that the contents of the intermediate compartment 10 can be visually inspected.

Manufacture of the Container

The composition of the front sheet 12, rear sheet 14 and third sheet 54, allow the creation of the peripheral seals and peelable seals using heat sealing techniques. Hot bars or dies are used at differing temperatures, pressures and application times to bring interfacing portions of the laminates employed to temperatures near or above melting to allow migration of material across the interface to form a bond of the desired strength and characteristics. For the bi-layer film comprising the front sheet 12 and Reynolds foil laminate comprising the rear sheet 14, a procedure for fabrication of the container 10 of the illustrative embodiment comprises cutting the front sheet to the desired dimensions for the container and cutting the aperture 32 for the outlet port 30. The outlet port in the embodiment shown in the drawings is injection molded and has a composition of 40% Fina Z9450 polypropylene copolymer and 60% Shell Kraton G4652 styrene butadiene elastomer. The outlet port is inserted through the aperture in the front sheet 12 and a heated die is employed to create the seal 36 of the front sheet adjacent the aperture to the flange 34 of the outlet port. A die temperature of 400° F. with a dwell time of 1.5 seconds under a pressure of 170 pounds per square inch (PSI) is used to accomplish the seal for the bilayer film and outlet port combination described previously. The third sheet 54 comprising the overlay for the intermediate compartment 20 is cut to size, positioned over the area to become the medicament compartment and attached to the front sheet 12 forming seals 25 and 27 using a die heated to 290° F. with a dwell time of 3.0 seconds under 70 PSI of pressure. The rear sheet 14 is cut to size and mated to the front sheet with the seal 16 around the peripheral edge created by a hot die at 330° F. with a dwell time of 25 seconds under 164 PSI of pressure.

The peelable seals 24 and 26 dividing the compartments in the container 10 are then created using double hot bars comprising a front bar in alignment with a rear bar constraining the elements of the container therebetween to form the seal thereby providing a substantially uniform seal across the container. The front bar contacting the previously combined third sheet 54 and front sheet 12 is maintained at a temperature of 265° F. The rear bar contacting the rear sheet 14 has a thin rubber covering to assure uniform application of pressure, and is maintained at 255° F. The double bars are maintained in contact with the front and rear sheets for 2 seconds with a pressure of 130 PSI. The peelable seals 24 and 26 as shown in FIG. 2 may be made individually with a single double bar set up or simultaneously with a twin double bar set up.

Without being bound by theory, it is thought that the peelability of the seals is obtained by limiting the time, pressure and temperature to that necessary to fuse the interface between the inner layers of the front and rear sheets which have a lower melting temperature than the intermediate and outer layers. The depth of the structural alteration in the inner layers in the fusion zone is limited, thereby imparting the peelable character to the seal while providing sufficient strength to prevent breakage in normal handling of the container. Higher temperatures and associated pressures and times are used for the peripheral seals and outlet seal, producing structure altering effects in a greater portion or depth of the sealing layers. Those skilled in the art will recognize various techniques for alternating the order of accomplishing the various seals and the orientation of the container 10 to allow filling the compartments with appropriate diluents and medicaments.

Preferred sealing parameters for several of the materials provided in various embodiments of the invention discussed previously with respect to Table I are shown in Table II.

TABLE II

Sealing parameters for laminate combinations

| | | | |
|---|---|---|---|
| Front Sheet (12) | S62-71 | S62-71 | S62-71 |
| Rear Sheet (14) | S62-101 | Foil | X62-053 |
| Medicament cover (54) | Foil | Foil | Foil |
| Edge Seal (16) | | | |
| Temp. (F) | 375 | 330 | 315 |
| Time (Sec) | 31 | 25 | 22.5 |
| Pressure (psi) | 218 | 164 | 218 |
| Peelable Seals (24, 26) | | | |
| Front bar (F) | 270 | 265 | 270 |
| Rear bar (F) | 270 | 255 | 260 |
| Time (sec) | 2 | 2 | 7 |
| Pressure (psi) | 130 | 130 | 130 |
| Medicament Cover Seals (25, 27) | | | |
| Temp. (F) | 290 | 290 | 290 |
| Time (sec) | 3 | 3 | 3 |
| Pressure (psi) | 70 | 70 | 70 |

Incorporating the sealing techniques described previously, filling of the container may be accomplished using several techniques. In an exemplary process employing the bi-layer film and Reynolds multi-layer foil laminate, a portion of the periphery comprising one side of the intermediate compartment 20 and a portion of one side of the upper compartment 18 are left unsealed for filling. The upper compartment 18 is then filled with liquid diluent through the opening. The unsealed portion of the periphery adjacent the compartment is then sealed using a hot die, e.g. at 265° F. with a dwell time of 5 seconds under 400 PSI pressure. The container is then autoclaved for sterilization. The intermediate compartment 20 is then dried and filled with a powder medicament and the edge adjacent the compartment 20 is then sealed using a hot die.

A production process for fabrication and filling of the container is anticipated to include the steps of fabrication of the outlet port and multi-layered laminate sheets, lamination of the peelable third sheet 54 foil to the clear front sheet 12, insertion and sealing of the outlet port 30 to the front sheet, fabrication of the container and seals employing a form, fill and seal process with filling of the diluent while leaving the intermediate powder compartment open, steam sterilization of the container 10 followed by aseptically drying, filling and sealing the powder compartment. Quality control inspection of the container and packaging for storage and shipment could then be accomplished.

USE OF THE CONTAINER

Figure 4:
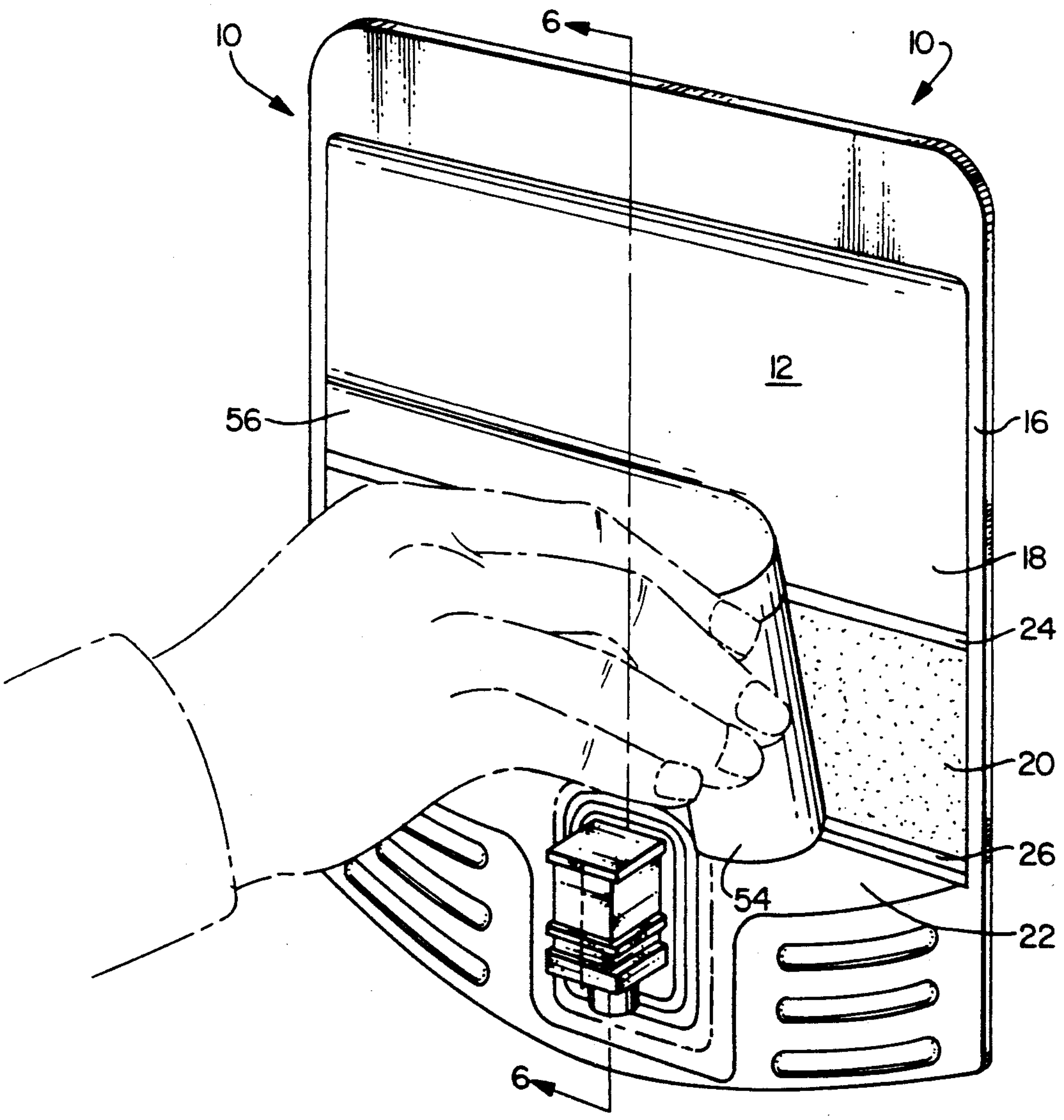
FIG. 4 is a semi-schematic pictorial view showing a peelable medicament compartment cover being removed for inspection of the medicament prior to mixing and use.
Figure 5:
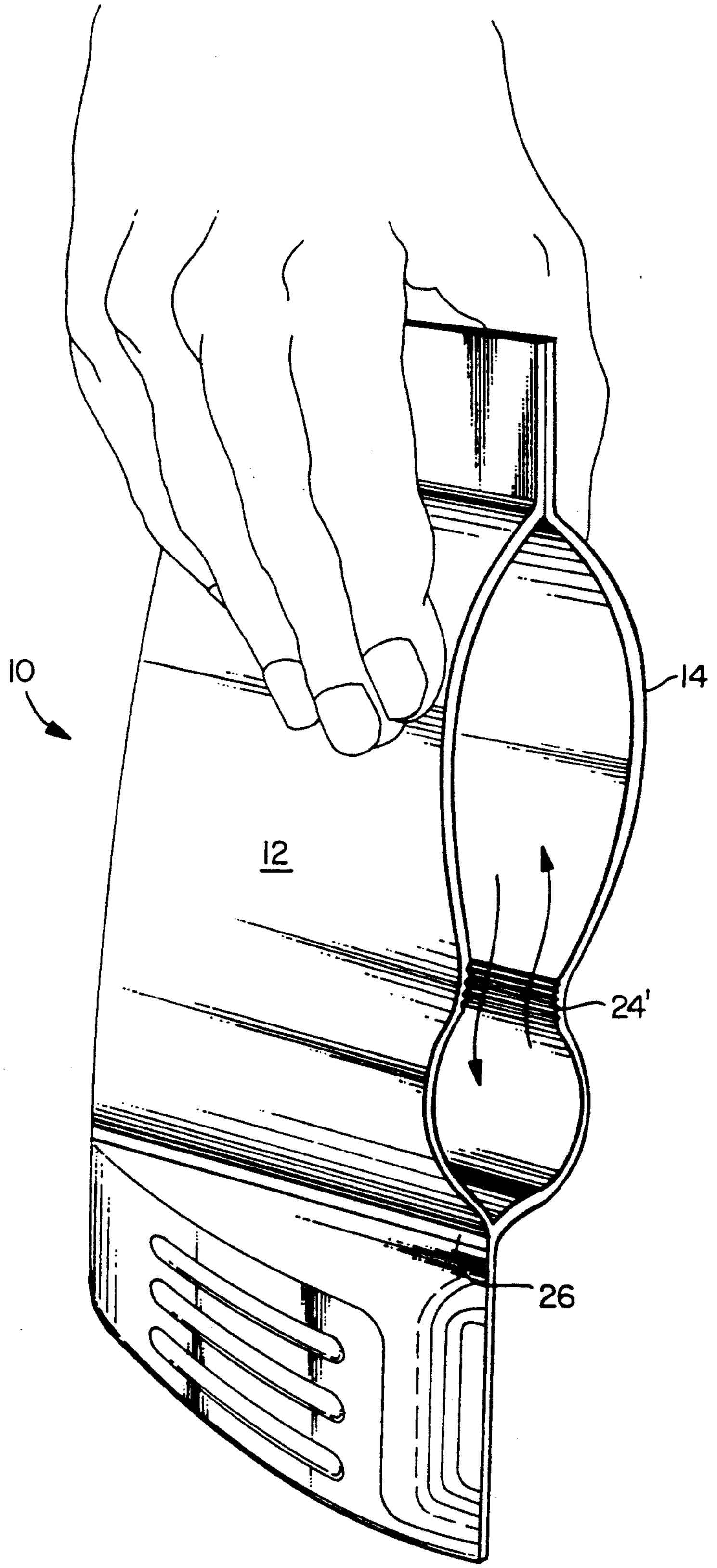
FIG. 5 is a semi-schematic pictorial cutaway demonstrating the manipulation of the container to separate the first peelable seal to mix the diluent and medicament.
Figure 6:
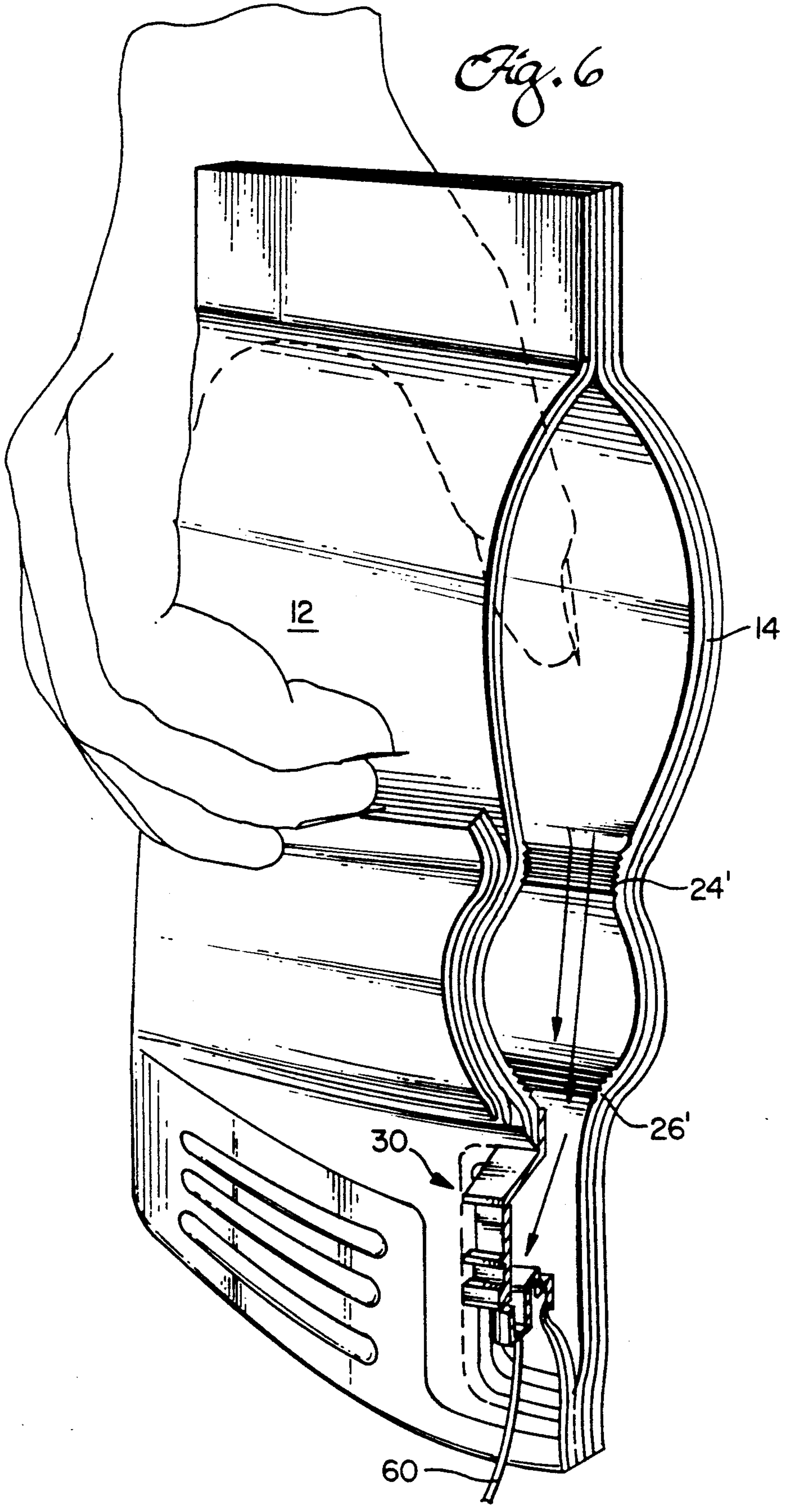
FIG. 6 is a semi-schematic pictorial cutaway demonstrating the manipulation of the container to separate the second peelable seal to dispense the medicated solution.

Use of the completed container is independent of the production technique employed. The triple compartmented container 10 and mixing system will be received by health care personnel in the completed configuration shown in FIGS. 1 and 2. Referring now to FIG. 4, in preparing to use the container, the medicament may be inspected by grasping the tab 56 on the third sheet 54 and peeling the third sheet from the container lo to enable visualization of the intermediate compartment 20 containing the powdered medicament. If the medicament appears dry and in normal condition, the solution can be mixed as shown in FIG. 5 by manipulating the container to compress the front and rear sheets in the area of the upper compartment 18. The pressure from the hydraulic forces created by manipulation of the container, ruptures the peelable seal between the upper and intermediate compartment (shown in the ruptured condition as 24'). Further manipulation by shaking causes mixing of the liquid diluent and the powdered medicament. Verification that complete mixing is obtained is made by visually observing the mixed solution. After complete mixing is accomplished, the peelable seal between the intermediate and lower compartment is broken as shown in FIG. 6 by again compressing the front and rear sheets of the container creating hydraulic pressure in the container to rupture the seal (shown in the ruptured condition as 26'). The solution is then dispensed from the container through the outlet port 30 using a standard IV delivery device 60.

The arrangement of the container 10 precludes delivery of unmixed diluent through the outlet port 30. Further, the arrangement of the intermediate compartment 20 between the diluent and outlet port enhances the probability of complete mixing and delivery of the medicament to the patient. For containers including a liquid diluent and powder medicament, rupture of the first peelable seal between the upper compartment 18 and intermediate compartment 20 is essentially assured prior to rupture of the second peelable seal between the intermediate compartment 20 and lower compartment 22 since the hydraulic forces developed in the diluent by manipulating the container cannot be transmitted through the powder in the intermediate compartment until the first seal has been ruptured and mixing of the diluent and powder has commenced. For those cases where a liquid medicament may be used, the relative size between the diluent compartment and the medicament compartment and the placement of the smaller compartment intermediate the larger compartment and the lower or outlet compartment assures development of hydraulic forces which will rupture the seal between the diluent and medicament compartments before rupture of the second seal with minimal care.

Those skilled in the art will recognize that the primary discussion of embodiments employing a liquid diluent and a single powdered medicament do not limit the scope of the invention. Use of liquid medicaments in an intermediate compartment or a plurality of compartments for powdered and liquid medicaments to be mixed with the diluent may be employed using the present invention.

Having now described in detail the invention as required by the patent statutes, those skilled in the art will recognize minor modifications or alterations to accomplish the specific applications. Such modifications and alterations are included within the scope and intent of the invention as described in the following claims.

What is claimed is:

1. A flexible container for combined storage and administration of medicament and diluent for IV solutions, the container comprising:
   - a flexible front sheet;
   - a flexible rear sheet sealed to the front sheet at a common peripheral edge;
   - a first peelable seal extending between two sides of the common peripheral edge and separably joining the front and rear sheet to form a compartment containing a diluent;
   - a second peelable seal extending between the two sides of the common peripheral edge and separably joining the front and rear sheet to form an outlet compartment and a compartment containing a medicament which is intermediate the outlet compartment and the diluent compartment, the outlet compartment being empty when the diluent and medicament are in their separate compartments, wherein the first peelable seal is rupturable by hydraulic pressure generated by manipulation of the diluent compartment, and wherein the diluent and medicament are mixed together by further manipulation of the container after rupture of the first peelable seal to form a diluent/medicament solution and thereafter the second peelable seal is rupturable by hydraulic pressure generated by further manipulation of the now joined diluent and medicament compartments so that the diluent/medicament solution can flow into the outlet compartment; and
   - an outlet port in communication with the outlet compartment, the outlet port engaging the front sheet whereby the rear sheet can fully collapse against the front sheet as the diluent/medicament solution is emptied from the container.

2. A flexible container as defined in claim 1 wherein the medicament is a dry powder.

3. A flexible container as defined in claim 1 wherein the flexible rear sheet is vapor impermeable.

4. A flexible container as defined in claim 3 wherein the front sheet comprises a transparent thermoplastic polymer.

5. A flexible container as defined in claim 4 wherein the surface of the front sheet adjoining the rear sheet comprises a blend of thermoplastic elastomer and polymer;
   and the surface of the rear sheet adjoining the front sheet comprises a polymer selected from the group consisting of polypropylene, polyethylene and a polypropylene - polyethylene copolymer.

6. A flexible container as defined in claim 5 wherein the rear sheet comprises:
   - a multi-layer laminate having
     - an inner layer of polypropylene interfacing with the front sheet;
     - an intermediate layer of aluminum foil; and
     - an outer layer of polyester.

7. A flexible container as defined in claim 6 wherein the front sheet comprises:
   - a bi-layer laminate having
     - an inner layer of a polypropylene - polyethylene co-polymer blended with styrene butadiene elastomer in about an 80%/20% ratio interfacing the rear sheet; and
     - an outer layer comprising polypropylene.

8. A container as defined in claim 7 wherein the polypropylene outer layer of the front sheet has a higher melting temperature than the inner layer of the front sheet.

9. A flexible container as defined in claim 4 wherein the interfacing layers of the front and rear sheets each comprise a thermoplastic elastomer.

10. A flexible container as defined in claim 4 wherein the interfacing layers of the front and rear sheets each comprise a polymer blended with styrene butadiene elastomer, the blend having a different percentage of styrene butadiene elastomer in the front and rear sheets.

11. A flexible container as defined in claim 5 further comprising:

a moisture impermeable cover sheet separably sealed to the front sheet, the cover sheet sized to extend over the medicament compartment.

12. A flexible container as defined in claim 11 wherein the cover sheet is a multi-layer laminate comprising:

a polypropylene copolymer layer adjacent the front sheet; an intermediate layer of aluminum foil; and an outer layer of polyester.

13. A flexible container for separately storing and mixing a liquid diluent and a medicament, the container comprising:

a flexible rear sheet having a thermoplastic material layer;

a flexible front sheet having a thermoplastic material layer adjacent the thermoplastic material layer of the rear sheet, the front sheet sealed to the rear sheet around a common peripheral edge;

at least two peelable seals extending across a width of a container to define at least three compartments in the container including a first compartment containing a liquid diluent;

a second compartment containing a medicament, the second compartment adjacent the first compartment; and a third outlet compartment adjacent either the diluent or the medicament compartment, wherein the outlet compartment is empty when the diluent and medicament are in the separable diluent and medicament compartments, a first of said peelable seals being between the diluent and medicament compartments and rupturable by means of a hydraulic force provided by compressing the rear sheet and front sheet in the area of the diluent compartment resulting in a mixture of the diluent and medicament, a second of said peelable seals adjacent the outlet compartment rupturable by means of a hydraulic force provided by compressing the front and rear sheets covering the diluent and medicament compartments to thereby admit the diluent/medicament mixture into the outlet compartment;

an outlet port in communication with the outlet compartment, the outlet port comprising means for enabling the front and rear sheets to fully collapse together as the diluent/medicament mixture is emptied from the container; and a moisture impermeable foil covering the medicament compartment, wherein at least a portion of the foil is removable for visual inspection of the medicament in said medicament compartment.

14. A flexible container as defined in claim 13 wherein the flexible front sheet is transparent.

15. A flexible container as defined in claim 13 wherein the flexible rear sheet comprises a multi-layer laminate including a layer of aluminum foil.

16. A flexible container as defined in claim 13 wherein the medicament is a dry powder.

17. A method for forming a flexible container for combined storage and administration of medicament and diluent for IV solutions, the method comprising the steps of:

providing a flexible, transparent, front sheet;

providing a flexible, vapor impermeable, rear sheet;

sealing the front and rear sheets together at a common peripheral edge, wherein the surface of the front sheet adjoining the rear sheet comprises a blend of thermoplastic elastomer and polymer and the surface of the rear sheet adjoining the front sheet comprises a polymer selected from the group consisting of polypropylene, polyethylene and a polypropylene - polyethylene copolymer;

heating the front and rear sheets in a first localized area to fuse together the heated portions of the adjoining surfaces, thereby forming a first peelable seal extending between two sides of the common peripheral edge, said first peelable seal separably joining the front and rear sheets to thereby form a first compartment for containing a diluent;

heating the front and rear sheets in a second localized area to fuse together the heated portions of the adjoining surfaces, thereby forming a second peelable seal extending between the two sides of the common peripheral edge, said second peelable seal separably joining the front and rear sheets to thereby form an outlet compartment and a compartment for containing a medicament, the medicament compartment being between the outlet compartment and the diluent compartment;

filling the diluent compartment with a diluent solution and filling the medicament compartment with a medicament, while leaving the outlet compartment empty;

wherein the first peelable seal is rupturable by hydraulic pressure generated by manipulation of the diluent compartment, and wherein after rupture of the first peelable seal, the diluent and medicament are mixed together by further manipulation of the container to form a diluent/medicament solution and thereafter the second peelable seal is rupturable by hydraulic pressure generated by further manipulation of the now joined diluent and medicament compartments so that the diluent/medicament solution can flow into the outlet compartment; and forming an outlet port in communication with the outlet compartment, the outlet port engaging the front sheet whereby the rear sheet is configured to fully collapse against the front sheet as the diluent/medicament solution empties from the container.

18. The method according to claim 17 comprising heating the front and rear sheets using a dual hot bar heat sealing apparatus having a front bar and a rear bar wherein the front bar temperature is higher than the rear bar temperature.

19. The method according to claim 17 wherein the medicament is a dry powder.

* * * * *

UNITED STATES PATENT AND TRADEMARK OFFICE

CERTIFICATE OF CORRECTION

PATENT NO. : 5,176,634

DATED : January 5, 1993

INVENTOR(S) : H. Theodore Young; Steven L. Smith

It is certified that error appears in the above-identified patent and that said Letters Patent is hereby corrected as shown below:

Column 8, line 65, change "1o" to -- 10 --;

Column 11, line 31, change "separable" to -- separate --.

Signed and Sealed this

Tenth Day of May, 1994

Attest:

Bruce Lehman

BRUCE LEHMAN

*Attesting Officer*

*Commissioner of Patents and Trademarks*